(12) United States Patent
Bertwell

(10) Patent No.: US 6,607,550 B1
(45) Date of Patent: Aug. 19, 2003

(54) METHOD OF TREATING NEUROPATHY USING A PHOTO ENERGY DEVICE

(75) Inventor: Dale E. Bertwell, Tampa, FL (US)

(73) Assignee: Anodyne Therapeutics, L.L.C., Denver, CO (US)

( * ) Notice: Subject to any disclaimer, the term of this patent is extended or adjusted under 35 U.S.C. 154(b) by 0 days.

(21) Appl. No.: 10/157,404

(22) Filed: May 29, 2002

Related U.S. Application Data
(60) Provisional application No. 60/317,587, filed on Sep. 6, 2001.

(51) Int. Cl.⁷ .............................................. A61N 5/006
(52) U.S. Cl. ........................... 607/88; 607/89; 607/90; 606/2; 128/898
(58) Field of Search ................ 606/2, 8, 9, 27; 607/88–92, 96–101; 128/898

(56) References Cited

U.S. PATENT DOCUMENTS

| | | | |
|---|---|---|---|
| 4,927,849 A | | 5/1990 | Caccia et al. |
| 4,930,504 A | * | 6/1990 | Diamantopoulos et al. . 128/395 |
| 5,066,676 A | | 11/1991 | Caccia et al. |
| 5,358,503 A | | 10/1994 | Bertwell et al. |
| 5,567,724 A | | 10/1996 | Kelleher et al. |
| 5,616,140 A | | 4/1997 | Prescott |
| 6,075,053 A | | 6/2000 | Hausheer |
| 6,087,392 A | | 7/2000 | Reiter |
| H1899 H | | 10/2000 | Bhat et al. |
| 6,302,900 B1 | * | 10/2001 | Riggs ........................ 607/89 |

OTHER PUBLICATIONS

Kochman et al., "Symptomatic Reversal of Peripheral Neuropathy in Patients with Diabetes." Journal of the American Podiatric Medical Association, Mar. 2002, 92 (3), pp. 125–130.*

Green et al., "Photon Stimulation: A New Form of Therapy for Chronic Diabetic Painful Neuropathy of the Feet." Pain Digest 1999: 9:286–291.*

Dr. DeSalvo, "Photonic Stimulator Therapy," Advanced Integrated Medical Center, Inc., http://www.desalvochiropractic.com/pdt.html, Sep. 20, 2000.*

*Design of Controlled Clinical Trials for Diabetic Polyneuropathy* from *Seminars in Neurology*–vol. 16, No. 2 by Anders A.F. Sima, M.D., Ph.D. and Charles Laudadio, M.D., Jun. 1996, pp. 187 to 191.

* cited by examiner

Primary Examiner—Linda C. M. Dvorak
Assistant Examiner—Ahmed Farah
(74) Attorney, Agent, or Firm—Greensfelder, Hemker & Gale, P.C.

(57) ABSTRACT

A method for the reduction of sensory impairment due to peripheral neuropathy comprising placing an apparatus which provides photo-energy in proximity to the skin and/or subcutaneous structures suffering from sensory impairment, and irradiating the skin and/or subcutaneous structures with the apparatus with sufficient duration (total weeks of treatments), intensity (energy in Joules per treatment) and frequency (treatments per week) to reduce sensory) impairment.

28 Claims, No Drawings

METHOD OF TREATING NEUROPATHY USING A PHOTO ENERGY DEVICE

The present application claims the benefit of provisional patent application number 60/317,587 filed Sep. 6, 2001.

The FIELD OF THE INVENTION

The field of the invention is the treatment of neuropathy. More specifically, the invention relates to the use of photo-energy treatment of neuropathy such as peripheral neuropathy, diabetic neuropathy, post-polio syndrome, small fiber neuropathy, amyotrophic lateral sclerosis (ALS), and multiple sclerosis (MS), wherein the neuropathy is treated and the sensory impairment of the patient is reduced.

BACKGROUND OF THE INVENTION

Neuropathy is a general term denoting functional disturbances and/or pathological changes in the peripheral nervous system. If the involvement is in one nerve it is called mononeuropathy, in several nerves, mononeuropathy multiplex, and if diffuse and bilateral, polyneuropathy. The etiology may be known, for example, arsenical neuropathy, diabetic neuropathy, ischaemic neuropathy or traumatic neuropathy, or it may be unknown.

Diabetic peripheral neuropathy is a consequence, in part, of diabetes mediated impairment blood flow to, and resultant hypoxia of nerves. The condition results in sensory impairment. Prior to the present invention, there was no known treatment for reversing the sensory impairment of this disease manifestation, although some treatments, such as capsiacin cream, tricyclic antidepressants, and valproic acid are efficacious in diminishing pain. Other studies have demonstrated some increase in conduction velocity with use of aldose reductase inhibitors. Insulin pumps or pancreas transplantation which reduce the hyperglycemia of diabetes are sometimes effective in slowing the progress of diabetic neuropathy. With each of these approaches there have been notable problems in feasibility, logistics, and efficacy, so that additional research into preventing/treating diabetic neuropathy has become a major research focus of the Juvenile Diabetes Foundation, the American Diabetes Association, and the National Institutes of Health.

Impaired sensation in the feet becomes evident to the patient and clinician several years after the onset of diabetes and, importantly, does not spontaneously regress. In other words, diabetic peripheral neuropathy is considered to be a progressive disease. Ultimately the loss of feeling can result in one or more ulcerations of the foot or feet. If the degree of sensory impairment reaches a level of 5.07 or higher, using the Semmes Weinstein monofilament test, there is a very high likelihood of ulceration, followed by amputation. Treatments that reduce sensory impairment may minimize the risk of the onset of ulcerations that often lead to amputations. Additionally, reduced sensory impairment may improve proprioception and balance, thereby reducing the likelihood of injurious falls.

Several products expected to reduce sensory impairment due to diabetic neuropathy, including nerve growth factor and aldose reductase inhibitors, in large clinical trials, have failed to meet full expectations of clinicians or patients. Prior to the present invention, there was no effective therapy available for reducing sensory impairment associated with diabetic neuropathy.

A number of pharmaceutical approaches have been taken to treat neuropathy, using medicaments to alleviate the symptoms. U.S. Pat. No. H1,899 to, Bhat, et al. discloses a method for determining a concentration of insulin-like growth factor-I (IGF-I) that defines a therapeutically effective dose of IGF-I. The patent discloses a dose that provides a therapeutic response in the treatment of neurological disorders for which IGF-I is utilized (including peripheral neuropathy, diabetic neuropathy, post-polio syndrome, small fiber neuropathy, arterial lateral sclerosis, and multiple sclerosis). The method comprises determining whether a particular dose of IGF-I causes a 1.5 fold or greater increase in the homeostatic concentration of plasma insulin-like growth factor binding proteins-2 (IGFBP-2) in a mammal that has previously received a defined dose of IGF-I. The method of the invention can also be used to determine whether or not biological tolerance has developed to a particular dose of IGF-I.

U.S. Pat. No. 6,087,392 to Reiter discloses a compound of (4-arylsulfonylamino)-tetrahydropyran-4-carboxylic acid hydroxamides which is useful in the treatment of a condition selected from the group of diseases including peripheral neuropathy. U.S. Pat. No. 6,075,053 to Hausheer discloses a method of treating patients afflicted with peripheral neuropathy by administering to a patient an effective amount of a thiol or reducible disulfide compound according to the formula set forth in the specification. U.S. Pat. No. 5,567,724 to Kelleher, et al. discloses a method of treating peripheral neuropathy using acid or alkaline phosphatase inhibitors.

U.S. Pat. Nos. 4,927,849 and 5,066,676 respectively to Caccia, et al. discloses sulfonamido derivatives having the property of inhibiting the aldose reductase enzyme system. Specific derivatives include xanthosulfonamido and benzensulfonamido derivatives, which are useful in the treatment of the complications induced by diabetes, such as those involving the eyes. The derivatives are also useful in the treatment of peripheral neuropathy.

All of the above patents require the patient to take pharmaceuticals or drugs, which involves ongoing treatments and possible side-effects. None of the above references teach or suggest the treatment of a patient having neuropathy that does not involve the use of pharmaceuticals or drugs, as does the present invention.

U.S. Pat. No. 4,930,504 discloses an array of a substantially monochromatic radiation source such as light-emitting diodes of a plurality of wavelengths, preferably three wavelengths, to treat inflammations, wounds, burns, chronic ulcerations including diabetic ulcers, deficient circulation, pain, nerve degeneration, eczema, shingles, infection, scars, acne bone fractures, muscle and ligament injuries, arthritis, osteo-arthritis, rheumatoidal arthritis, skin grafts, gingival irritation, oral ulcers, dental pain and swelling, cellulitis, stretch marks, skin tone, alopecia areata, trigeminal neuralgia, herpes, zosten, sciatica, cervical erosions and other conditions. However, this patent does not disclose that a photo-energy source may be capable of reducing sensory impairment associated with neuropathy.

The use of monochromatic infrared energy has been successfully used to treat recalcitrant dermal lesions, including venous ulcer, diabetic ulcers, and a wound related to scleroderma. (Horwitz, L. R., Advances in Wound Care, January/February, 1999). U.S. Pat. No. 5,358,503 discloses a device for the treatment of skin and subcutaneous structures with photo-energy and * therapeutic heat. The device includes a flexible pad which holds diodes in juxtaposed position with each other. Neither the Horwitz article nor U.S. Pat. No. 5,358,503, disclose the use of an apparatus for the reduction of sensory impairment associated with neuropathy.

None of the above references disclose the present invention involving the use of an apparatus for photo-energy treatment for reducing sensory impairment due to neuropathy.

SUMMARY OF THE INVENTION

The present invention is a method for the reduction of sensory impairment due to peripheral neuropathy comprising placing an apparatus which provides photo-energy in proximity to the skin and/or subcutaneous structures suffering from sensory impairment, arid irradiating the skin and/or subcutaneous structures with the apparatus with sufficient duration. (total weeks of treatments), intensity (energy in Joules per treatment) and frequency (treatments per week) to reduce sensory impairment. The reduction in sensory impairment can be measured by the Semmes Weinstein test and/or other diagnostic-type test of sensory impairment. Optionally, the apparatus may also deliver therapeutic heat so that the treatment area of the skin and the adjacent subcutaneous structure of the patient receive photo energy treatment and thermal treatment simultaneously or selectively.

DETAILED DESCRIPTION OF THE INVENTION

A variety of apparatuses can be used to generate the photo-energy needed for treatments that reduce sensory impairment. The preferred apparatus for photo-energy treatment is a plurality of diodes, defining a treatment area, each diode having a longitudinal axis and being capable of projecting a non-coherent cone of photo-energy when energized. The cone of photo-energy from each diode overlaps the cone of photo-energy from each other diode, so that the photo-energy completely covers the treatment area. The apparatus has a means for holding each of said diodes in position with each other and in proximity of the skin in substantially perpendicular relationship to said longitudinal axis.

Such means include a flexible resin-based pad, such as a polyacrylate pad, an interconnecting flexible mesh pad, a woven cloth-like material pad, a deformable matrix, such as modeling clay which can conform to an extremity, a castable material which hardens to a desired shape, or a flexible elongated strip of cloth or resin-based material that can be wrapped around a digit or directed to a small, narrow area.

The apparatus has means connected to the diodes for activating them. Such means includes switches, such as manually activated switches, and electronic switches, such as solenoids, which can be activated manually, or electronically, such as by a microprocessor. The present invention includes using an apparatus, wherein the apparatus is attached to a microprocessor which is programmed to activate and deactivate the apparatus.

Optionally, the apparatus may also deliver therapeutic heat so that the treatment area of the skin and the adjacent subcutaneous structure of the patient receive photo-energy treatment and thermal treatment simultaneously or selectively. The means for heating includes the diodes themselves, wherein the heating provided is increased with the current provided. Further heating can be provided by resistance heating, such as by resistors or heating elements.

The preferred apparatus for photo-thermal treatment is described in detail in U.S. Pat. No. 5,358,503, which is hereby incorporated by reference.

Sensory impairment can be measured by a variety clinical diagnostic of tests. The most common test is the Semmes Weinstein test, where pressure is applied against the skin of affected areas using monofilaments of varying thicknesses to determine the level of sensory impairment. Other methods of determining sensory impairment include the hot-versus-cold test which is used to test sensory impairment to temperature change. The vibratory test is used to test sensory impairment to a vibrating tuning fork. The nerve conduction velocity test (NCV) measures sensory impairment by evaluating the conductivity of nerves, as does the needle electromylagram test (EMG). The quantitative sensory test gives a two point discrimination test of sensory impairment. The Romberg test is used to determine gross sensory impairment of the lower extremities as it affects balance, and the Balance Master is a device that measures gross sensory impairment of the lower extremities affecting balance in more objective terms. Other quantitative tests of sensory impairment due to neuropathy may be employed or developed in the future. Any one of these tests, alone or in combination could indicate sensory impairment resulting from neuropathy. A preferred diagnostic test is the Semmes Weinstein monofilament test.

The present method involves a sequential treatment, wherein a patient is treated at a frequency of from about one to fourteen times each week for a period of about from about five to sixty minutes a treatment. Transitory response may be observed after one treatment and longer lasting response may require additional treatments, which, in neuropathy due to a chronic condition, may be required for a period coextensive with the remainder of the patient's life. A preferred frequency is from about one to fourteen treatments weekly with a duration of from ten to fifty minutes. The total number of treatments can range from about one to 150. The patient is treated for a duration of from about one to twelve weeks. A preferred range of duration is from about two to ten weeks. The frequency and duration of treatment, as well as the total number of treatments, depends, in part, on the severity and duration of the neurological impairment as Well as the chronicity of the underlying causation of neuropathy.

The intensity of the treatment can be changed by varying the Joules of photo-energy delivered to the treatment site. Typically, from about 1450 to about 6500 Joules are delivered per affected extremity per treatment, however, fewer Joules per treatment delivered more frequently, i.e., a lower intensity with a higher frequency, may be equally effective.

The intensity of the photo-energy delivered in a treatment is calculated as the Joules per treatment. It is calculated as the product of the energy (Joules) per area ($cm^2$) per minute emitted by the photo-energy device, the treatment area ($cm^2$), and the length (minutes) of treatment. Variance in the energy emitted by the photo-energy device, the treatment area ($cm^2$), and the length of treatment (minutes) will accordingly change the intensity of the photo-energy delivered as measured in Joules per treatment. The preferred photo-energy device delivers about 1.15 Joules per $cm^2$ per minute ($J/cm^2/min$) over the defined treatment area of about 22.5 $cm^2$. As many as eight photo-energy devices may be used simultaneously to provide a treatment area of up to 180 cm$^2$. Thus, a treatment using from one to eight photo-energy devices will yield a range of from about 26 to about 207 Joules per minute of treatment. Using a treatment time of about 30 minutes, the intensity of treatment would be from about 780 to about 6240 J/treatment. The intensity of the treatment of the present invention is in the range of from about 500 to about 7000 J/treatment. A preferred range is from about 500 to about 5000 J/treatment. A most preferred range is from about 1500 to about 5000 J/treatment.

The present invention further embodies the use of the above method in a prophylactic manner, so as to prevent a neurological deficit in patients afflicted with progressive chronic conditions, such as diabetes, from which neuropathy is known to eventually occur. In such circumstances, the treatment of chronic conditions will have a duration that spans the life of the patient. Alternatively, the treatment maybe subsequent to an initial series of treatments, and long-term to prevent the re-occurrence of sensory impairment, with the duration ranging up to the life-span of the patient.

EXAMPLES OF THE INVENTION

The following examples of the invention are made to illustrate the invention and are not to limit in any manner the scope of the invention, as embodied in the claims. Generally, the results of clinical tests are evaluated statistically to determine significance using what is known as a P value. For example, a P value of 0.05 indicates that there is a 5% probability that the determined relationship between the variables (i.e., between the treatment and the observed affects) in the study are by pure chance. A P value of less than 0.05 is deemed clinically significant, and the lower the P value, the greater the statistical validity.
Study 1

Methods and Materials

Forty-nine patients were treated at The Medical Center of Aurora, a HealthOne facility, Aurora, Co. in the Physical Therapy Department. The patients ranged in age from 35 to 80 years old; 25 were Type I diabetic patients and 24 were Type II diabetic patients. All had neuropathy based on the Semmes Weinstein (SW) monofilament test which measures the ability of the patient to feel a monofilament applied to their skin. In addition, the ability to detect hot-versus-cold (H/C) was also absent or impaired in each patient. No treatments or pharmaceuticals that would have modified circulation in the lower extremities were employed during the 30 days prior to beginning this study. No changes were made in the standard of medical care associated with diabetes for these subjects, including insulin or oral hypoglycemic agents, diet, blood pressure medications, and exercise. Forty-nine (49) diabetic subjects whose SW, H/C, and gait analysis (the patient's ability to walk normally) values were abnormal were treated.

Procedure

Photo-energy was delivered from a series of 60 gallium aluminum arsenide diodes in a flexible pad (diode array) placed on the patient's feet and/or lower leg. Four diode pads (60 diodes in each pad) were used during the treatment of each lower extremity. Each treatment was for 30 minutes. The intensity of the treatments was about 3100 J/treatment of the lower, extremity, which was delivered over a treatment area of about 90 cm$^2$. One diode pad was placed on the distal posterior aspect of the patient's tibia, and another diode array was placed over the patient's anterior distal tibia. One pad was placed on the dorsal and another on the ventral surface of the patient's foot. This was done to each foot. An alternate pad placement was used specifically at the plantar aspect of each foot if the posterior tibia region was uncomfortable for some subjects. Each subject received a total of 12 treatments having a duration of 30 minutes that were administered three times a week for one month.

Several sizes of Semmes Weinstein monofilaments (3.22, 3.84, 4.08, 4.17, 4.31, 4.56, 4.74, 4.93, 5.07, 5.18, 5.46, 5.88, 6.10, and 6.45) were applied to at least three areas of the plantar side of the feet. As far as possible, the same locations were tested at each visit. The filament was applied until it began to bend, and was held in place for approximately 1.5 seconds. Each site was tested three times. Care was taken to test areas that had the least thickness of the keratin layer. The test sites were the great toe, plantar arch region, and the fourth toe. The response to the filament testing was based on the subjective response from the patient of "NOW" when the patient could feel the filament. Hot/cold testing was also done at the same test sites. Response to the hot/cold testing was determined from subjective reports of whether the patient could sense the hot or cold bar. These were graded as absent, impaired, or intact.

The data for Type I and Type II diabetic patients were grouped and analyzed by repeated measured analysis; values reported are means±standard deviation (SD). The statistical significance, expressed as the P value, was P<0.001.
Results The ages of subjects, Type of diabetes (I or II), SW values, and hot/cold (H/C) detection ability prior to beginning the study and after photo energy treatment are shown in Tables 1 and 2. Type I diabetic patients (60.4±12.8 years old) were approximately 12 years younger than the Type II diabetic subjects (72.5±5.5 years old).

Baseline SW deficits were virtually identical in the Type I (mean±SD: 5.49±0.52) and Type II (mean±SD: 5.44±0.47) (Table 1). Thirteen Type I diabetic subjects and 13 Type II diabetic subjects had absent sensation to H/C prior to treatment.

Reduction in sensory impairment was noted after six treatments and further improvement was noted over six additional treatments. After 12 [photo-energy treatments, 100% of the Type I subjects had Semmes Weinstein monofilament values below 5.07. Mean Semmes Weinstein values for all 25 Type I subjects were 4.26±0.34 after twelve treatments. A similar response to photo-energy treatment in Type II diabetic subjects was observed. Specifically, after 12 treatments with photo-energy, 100% of the Type II subjects had Semmes Weinstein values below 5.07, and the mean for all 24 subjects was 4.45±0.32. The mean (±SD) SW values before and after 12 treatments with photo-energy for all diabetic subjects are shown in Table 1.

Before treatment, none of the subjects (Type I or Type II) had intact ability to discriminate hot from cold (Table 2). After 12 treatments with the photo-energy device, all the subjects converted from absent and impaired H/C sensation to impaired and intact ability to discriminate hot from cold (Table 2).

TABLE 1

Subject characteristics,
Semmes Weinstein (SW) monofilament.
SW Monofilament Values

| Diabetes Type | N | Age | Baseline | 6 Treatments | 12 Treatments |
|---|---|---|---|---|---|
| Type I | 25 | 60 ± 12 | 5.49 ± 0.52 | 4.74 ± 0.38 | 4.26 ± 0.34* |
| Type II | 24 | 72 ± 5 | 5.44 ± 0.47 | 4.84 ± 0.36 | 4.45 ± 0.32* |

TABLE 2

Subject characteristics,
hot/cold sensation deficits.
Hot/Cold

| | Baseline | | | After 12 Treatments | | |
|---|---|---|---|---|---|---|
| Diabetes | Absent | Impaired | Intact | Absent | Impaired | Intact |
| Type I | 13 | 12 | 0 | 0 | 16 | 9 |
| Type II | 13 | 11 | 0 | 0 | 30 | 4 |

N = number of subjects
Values are Mean ± Standard Deviation
Baseline = patient characteristics before treatment with MIRE
SW = Semmes Weinstein monofilament
*P < 0.0001 vs. control The examples demonstrate that photo-energy treatments using the photo energy device with the desired frequency, duration and intensity reduced sensory impairment in diabetic patients, as measured by the Semmes Weinstein test and the hot/cold sensation test.

Study 2

Eight patients exhibiting sensory impairment due to neuropathy as the inability to sense the Semmes Weinstein 5.07 monofilament at three tested sites on both feet received treatments with [photo energy]—photo-energy—to determine whether sensory impairment was reduced after treatment. Each patient served as their own control, receiving treatment on only one foot initially. The patients received 12 treatments for 30 minutes to an area of about 45 cm$^2$ delivering a photo-energy intensity of approximately 1550J/treatment over a period of about one month. At the conclusion of treatment of the first foot (Part I of the study), the second foot was treated with the same protocol (Part II of the, study). Fifteen lower extremities were evaluated since one patient withdrew from the study after successfully completing treatment on the first foot.

Results

Part I

At the conclusion of the treatments, all of the actively treated feet (n=8) obtained a reduction in sensory impairment as measured at one or more pre-tested sites by the Semmes Weinstein. 5.07 monofilament test. At that point, one patient purchased the photo energy device, and withdrew from the study. None of the control feet (n=8) obtained any reduction in sensory impairment as measured at three pre-tested sites by the Semmes Weinstein 5.07 monofilament test.

Part II

At the conclusion of treatments of the second (control) feet (n=7), all of the feet obtained a reduction in sensory impairment as measured at one or more pre-tested sites as measured by the Semmes Weinstein 5.07 monofilament test.

Each foot was found to have a reduction of sensory impairment after treatment according to the claimed method.

Study 3

Ten patients exhibiting sensory impairment due to neuropathy as tested by the inability to sense the Semmes Weinstein 5.07 monofilament test at three sites on both feet received treatments with photo-energy. The patients received ten treatments over a one month period on an area of about 45 cm$^2$ with an intensity of about 1550 J/treatment. Nine patients Were treated on both feet, and one patient Was treated on one foot. One other patient received only nine treatments.

Results

The patient treated on one foot experienced a reduction of sensory impairment, purchased the photo-energy device and dropped out of the study. Of the remaining nine patients, all of the actively treated feet (n=19) obtained a reduction of sensory impairment as measured at one or more of the pre-tested sites by the Semmes Weinstein 5.07 monofilament test.

Study 4

Eight patients exhibiting sensory impairment due to neuropathy, as tested by the Semmes Weinstein 5.07 monofilament test at from, three to five sites on both feet received treatment with photo-energy on one foot, and a placebo treatment of the second foot. The test was double-blind, in that neither the patient nor the evaluator knew which was the placebo. The patients received one treatment for 45 minutes over a treatment area of about 90 cm$^2$, with a photo-energy intensity of about 6500 J/treatment.

Results

All of the actively treated feet (n=8) obtained reduction in sensory impairment as measured by the Semmes Weinstein monofilament test at all the pre-tested sites. Of the placebo treated feet (n=8), six of the eight experienced no reduction in sensory impairment, and two obtained some reduction in sensory impairment at several of the pre-tested sites.

Additional studies have been made, further supporting the results of this study. A follow-up evaluation of the treated patients indicated that the reduced sensory impairment Was less evident with time. This data indicates a long-term therapy involving photo-energy may be necessary to maintain reduced sensory impairment at the desired levels.

What is claimed is:

1. A method of treatment for reducing sensory impairment due to neuropathy comprising placing an apparatus for photo-energy treatment in proximity of skin or subcutaneous structures suffering from sensory impairment, wherein the apparatus is in sufficient proximity to irradiate the skin or subcutaneous structures with sufficient duration, intensity and frequency of treatment to observe reduced sensory impairment, wherein the apparatus comprises a plurality of diodes, defining a treatment area, each diode having a longitudinal axis and being capable of projecting a non-coherent cone of light when energized, the cone of light from each diode overlapping the cone of light from each other diode so that the light completely covers the treatment area;

means for holding each of said diodes in position with each other and in proximity of the skin in substantially perpendicular relationship to said longitudinal axis; and means connected to said diodes for activating them;

wherein the frequency of treatment is from about one to 14 times a week.

2. The method of claim 1, wherein the reduction in sensory impairment can be determined by the Semmes Weinstein test.

3. The method of claim 1, wherein the neuropathy is a chronic condition and treatments are given at a frequency of about one to 14 times a week for a period with a duration of the patient's lifetime, and at an intensity of from about 500 to about 7000 J/treatment.

4. The method of claim 1, wherein the duration of treatment is from about one to ten weeks.

5. The method of claim 4, wherein the intensity of treatment is from about 500 to about 7000 J/treatment.

6. A method of treatment for reducing sensory impairment due to neuropathy comprising placing an apparatus for photo-energy treatment in proximity of skin or subcutaneous structures suffering from sensory impairment, wherein the apparatus is in sufficient proximity to irradiate the skin or subcutaneous structures with sufficient duration, intensity and frequency of treatment to observe reduced sensory impairment, and wherein the apparatus has means for activating it a plurality of diodes, defining a treatment area, each diode having a longitudinal axis and being capable of projecting a non-coherent cone of light when energized, the cone of light from each diode overlapping the cone of light from each other diode so that the light completely covers the treatment area;

means for holding each of said diodes in position with each other and in proximity of the skin in substantially perpendicular relationship to said longitudinal axis; and means connected to said diodes for activating them.

7. A method for the treatment of diabetic peripheral neuropathy to reduce sensitivity impairment comprising placing an apparatus for photo-energy treatment in proximity of skin or subcutaneous structures suffering from peripheral neuropathy, wherein the apparatus is in sufficient proximity to irradiate the skin or subcutaneous structures with sufficient duration, intensity and frequency of treatment to treat the neuropathy and observe reduction in sensory impairment as indicated by a clinical test, wherein the apparatus comprises a plurality of diodes, defining a treatment area, each diode having a longitudinal axis and being capable of projecting a non-coherent cone of light when energized, the cone of light from each diode overlapping the cone of light from each other diode so that the light completely covers the treatment area;

means for holding each of said diodes in position with each other and in proximity of the skin in substantially perpendicular relationship to said longitudinal axis; and means connected to said diodes for activating them.

8. A method of treatment for reducing sensory impairment due to neuropathy comprising placing an apparatus for photo-energy treatment in proximity of skin or subcutaneous structures suffering from sensory impairment, wherein the apparatus is in sufficient proximity to irradiate the skin or subcutaneous structures with sufficient duration, intensity and frequency of treatment to observe reduced sensory impairment; wherein the apparatus comprises:

a plurality of diodes, defining a treatment area, each diode having a longitudinal axis and being capable of projecting a non-coherent cone of light when energized, the cone of light from each diode overlapping the cone of light from each other diode so that the light completely covers the treatment area;

means for holding each of said diodes in position with each other and in proximity of the skin in substantially perpendicular relationship to said longitudinal axis; and means connected to said diodes for activating them;

wherein the frequency of treatment is from about one to 14 times a week;

wherein the duration of treatment is from about one to twelve weeks; and wherein the intensity of treatment is from about 500 to about 7000 J/treatment.

9. A method for the treatment of diabetic peripheral neuropathy to reduce sensitivity impairment comprising placing an apparatus for photo-energy treatment in proximity of skin or subcutaneous structures suffering from peripheral neuropathy, wherein the apparatus is in sufficient proximity to irradiate the skin or subcutaneous structures with sufficient duration, intensity and frequency of treatment to treat the neuropathy and observe reduction in sensory impairment as indicated by a clinical test; wherein the frequency of treatment is from about one to 14 times a week.

10. The method of claim 9, wherein the apparatus comprises a plurality of diodes, defining a treatment area, each diode having a longitudinal axis and being capable of projecting a non-coherent cone of light when energized, the cone of light from each diode overlapping the cone of light from each other diode so that the light completely covers the treatment area;

means for holding each of said diodes in position with each other and in proximity of the skin in substantially perpendicular relationship to said longitudinal axis; and means connected to said diodes for activating them.

11. The method of claim 9, wherein the reduction in sensory impairment can be determined by the Semmes Weinstein monofilament test.

12. A method of treatment of diabetic peripheral neuropathy to reduce sensory impairment comprising placing an apparatus for photo-energy treatment in proximity of skin or subcutaneous structures suffering from sensory impairment, wherein the apparatus is in sufficient proximity to irradiate the skin or subcutaneous structures with sufficient duration, intensity and frequency of treatment to observe reduced sensory impairment, wherein the apparatus comprises a plurality of diodes, defining a treatment area, each diode having a longitudinal axis and being capable of projecting a non-coherent cone of light when energized, the cone of light from each diode overlapping the cone of light from each other diode so that the light completely covers the treatment area;

means for holding each of said diodes in position with each other and in proximity of the skin in substantially perpendicular relationship to said longitudinal axis; and means connected to said diodes for activating them;

wherein the frequency of treatment is from about one to 14 times a week;

wherein the duration of treatment is from about one to twelve weeks; and wherein the intensity of treatment is from about 500 to about 7000 J/treatment.

13. The method of claim 12, wherein the apparatus further comprises means for heating each of said diodes so that the treatment area of the skin and the adjacent subcutaneous structure of the patient receive light treatment and thermal treatment simultaneously or selectively and means connected to said heating means for activating them.

14. The method of claim 12, wherein continuing treatments are delivered with sufficient duration, intensity and frequency that the observed reduction in sensory impairment does not reoccur.

15. A method of treatment for reducing sensory impairment due to neuropathy comprising
   a) testing a patient to determine sensory impairment;
   b) placing an apparatus for photo-energy treatment in proximity of skin or subcutaneous structures suffering from sensory impairment, wherein the apparatus is in sufficient proximity to irradiate the skin or subcutaneous structures with sufficient duration, intensity and frequency of treatment to reduce sensory impairment; and
   c) determining reduced sensory impairment by subsequent testing, wherein the apparatus has means for activating it.

16. The method of claim 15, wherein the apparatus comprises
   a plurality of diodes, defining a treatment area, each diode having a longitudinal axis and being capable of projecting a non-coherent cone of light when energized, the cone of light from each diode overlapping the cone of light from each other diode so that the light completely covers the treatment area;
   means for holding each of said diodes in position with each other and in proximity of the skin in substantially perpendicular relationship to said longitudinal axis; and
   means connected to said diodes for activating them.

17. The method of claim 15, wherein the sensory impairment can be determined by the Semmes Weinstein test.

18. A method of treatment for reducing sensory impairment due to neuropathy comprising
   a) testing a patient to determine sensory impairment;
   b) placing an apparatus for photo-energy treatment in proximity of skin or subcutaneous structures suffering from sensory impairment, wherein the apparatus is in sufficient proximity to irradiate the skin or subcutaneous structures with sufficient duration, intensity and frequency of treatment to reduce sensory impairment; and
   c) determining reduced sensory impairment by subsequent testing, wherein the apparatus comprises:
      a plurality of diodes, defining a treatment area, each diode having a longitudinal axis and being capable of projecting a non-coherent cone of light when energized, the cone of light from each diode overlapping the cone of light from each other diode so that the light completely covers the treatment area;
      means for holding each of said diodes in position with each other and in proximity of the skin in substantially perpendicular relationship to said longitudinal axis; and
      means connected to said diodes for activating them.

19. The method of claim 18, wherein the apparatus further comprises means for heating each of said diodes so that the treatment area of the skin and the adjacent subcutaneous stricture of the patient receive light treatment and thermal treatment simultaneously or selectively and means connected to said heating means for activating them.

20. The method of claim 18, wherein continuing treatments are delivered with sufficient duration, intensity and frequency that the observed reduction in sensory impairment does not reoccur.

21. A method for the treatment of diabetic peripheral neuropathy to reduce sensitivity impairment comprising placing an apparatus for photo-energy treatment in proximity of skin or subcutaneous structures suffering from peripheral neuropathy, wherein the apparatus is in sufficient proximity to irradiate the skin or subcutaneous structures with sufficient duration, intensity and frequency of treatment to treat the neuropathy and observe reduction in sensory impairment as indicated by a clinical test, wherein the apparatus comprises
   a plurality of diodes, defining a treatment area, each diode having a longitudinal axis and being capable of projecting a non-coherent cone of light when energized, the cone of light from each diode overlapping the cone of light from each other diode so that the light completely covers the treatment area;
   means for holding each of said diodes in position with each other and in proximity of the skin in substantially perpendicular relationship to said longitudinal axis; and
   means connected to said diodes for activating them, wherein the frequency of treatment is from about one to 14 times a week.

22. The method of claim 21, wherein the duration of treatment is from about one to ten weeks.

23. The method of claim 22, wherein the intensity of treatment is from about 500 to about 7000 J/treatment.

24. A method of treatment for reducing sensory impairment due to neuropathy comprising
   a) testing a patient to determine sensory impairment;
   b) placing an apparatus for photo-energy treatment in proximity of skin or subcutaneous structures suffering from sensory impairment, wherein the apparatus is in sufficient proximity to irradiate the skin or subcutaneous structures with sufficient duration, intensity and frequency of treatment to reduce sensory impairment; and
   c) determining reduced sensory impairment by subsequent testing, wherein the apparatus comprises a plurality of diodes, defining a treatment area, each diode having a longitudinal axis and being capable of projecting a non-coherent cone of light when energized, the cone of light from each diode overlapping the cone of light from each other diode so that the light completely covers the treatment area;
      means for holding each of said diodes in position with each other and in proximity of the skin in substantially perpendicular relationship to said longitudinal axis; and
      means connected to said diodes for activating them; wherein the frequency of treatment is from about one to 14 times a week.

25. The method of claim 24, wherein the duration of treatment is from about one to ten weeks.

26. The method of claim 25, wherein the intensity of treatment is from about 500 to about 7000 J/treatment.

27. A method for the treatment of diabetic peripheral neuropathy to reduce sensitivity impairment comprising placing an apparatus for photo-energy treatment in proximity of skin or subcutaneous structures suffering from peripheral neuropathy, wherein the apparatus is in sufficient proximity to irradiate the skin or subcutaneous structures with sufficient duration, intensity and frequency of treatment to treat the neuropathy and observe reduction in sensory impairment as indicated by a clinical test, wherein the reduction in sensory impairment can be determined by the Semmes Weinstein monofilament test.

28. A method of treatment for reducing sensory impairment due to neuropathy comprising a) testing a patient to determine sensory impairment;

b) placing an apparatus for photo energy treatment in proximity of skin and/or subcutaneous structures suffering from sensory impairment, wherein the apparatus is in sufficient proximity to irradiate the skin and/or subcutaneous structures with sufficient duration, intensity and frequency of treatment to reduce sensory impairment; and c) determining reduced sensory impairment by subsequent testing, wherein the sensory impairment can be determined by the Semmes Weinstein test.

* * * * *